(12) United States Patent
Tange et al.

(10) Patent No.: US 6,989,548 B2
(45) Date of Patent: Jan. 24, 2006

(54) INSPECTION DEVICE FOR METAL RINGS OF A CONTINUOUSLY VARIABLE TRANSMISSION BELT

(75) Inventors: Hiroshi Tange, Fuji (JP); Ushio Suzuki, Aichi (JP)

(73) Assignees: JATCO Ltd., (JP); Fuji Opto Co., Ltd., (JP)

( * ) Notice: Subject to any disclaimer, the term of this patent is extended or adjusted under 35 U.S.C. 154(b) by 0 days.

(21) Appl. No.: 11/090,016

(22) Filed: Mar. 28, 2005

(65) Prior Publication Data

US 2005/0222812 A1  Oct. 6, 2005

(30) Foreign Application Priority Data

Mar. 29, 2004 (JP) .............................. 2004-097229

(51) Int. Cl.
 *G01N 21/88*  (2006.01)
(52) U.S. Cl. .......................... 250/559.45; 250/559.46; 250/559.42; 356/430; 356/237.2
(58) Field of Classification Search ............... 250/221, 250/223 B, 559.4, 559.41, 559.42, 559.43, 250/559.45, 559.46

See application file for complete search history.

(56) References Cited

U.S. PATENT DOCUMENTS 4,659,937 A * 4/1987 Cielo et al. ............. 250/559.24
6,613,334 B2 * 9/2003 Yoshida et al. ............. 474/242

FOREIGN PATENT DOCUMENTS

JP   09-304288   11/1997
JP   11-248637   9/1999

* cited by examiner

*Primary Examiner*—Kevin Pyo
(74) *Attorney, Agent, or Firm*—Blank Rome LLP (57) ABSTRACT

An inspection device for metal rings of a Continuously Variable Transmission (CVT) V-belt which does not perform excessive detection of gloss marks as a detrimental manufacturing flaw configured with a first low-pass cutting portion for cutting out a predetermined low-frequency component contained in an electrical signal outputted from a first light detector or an electrical signal correlated to its electrical signal and a second low-pass cutting portion for cutting out a predetermined low-frequency component contained in an electrical signal outputted from a second light detector or an electrical signal correlated to its electrical signal, which precede a difference value calculation portion. The difference value calculation portion calculates a difference value between an electrical signal which passes through the first low-pass cutting portion and an electrical signal which passes through the second low-pass cutting portion.

2 Claims, 5 Drawing Sheets

MOVEMENT DIRECTION

FIG. 4B

Sd
(WHEN BAND PASS FILTER SECTION 45 IS NOT PROVIDED)

→ TIME

FIG. 4C

NO SIGNAL GENERATED BY A GLOSS MARK

Sd
(WHEN BAND PASS FILTER 45 IS PROVIDED)

→ TIME

FIG. 5

INSPECTION DEVICE FOR METAL RINGS OF A CONTINUOUSLY VARIABLE TRANSMISSION BELT

BACKGROUND OF THE INVENTION

1. Field of the Invention

The present invention relates to an inspection device for metal rings. More particularly, the present invention relates to an inspection device for metal rings which are parts that constitute a V-belt type of a Continuously Variable Transmission belt (hereinafter referred to as "CVT belt").

2. Description of the Related Art

Conventionally, there is a known CVT belt structure which laminates a plurality of thin metal rings in a stack of approximately 0.2 mm in thickness to which steel elements are consecutively attached.

Figure 5:
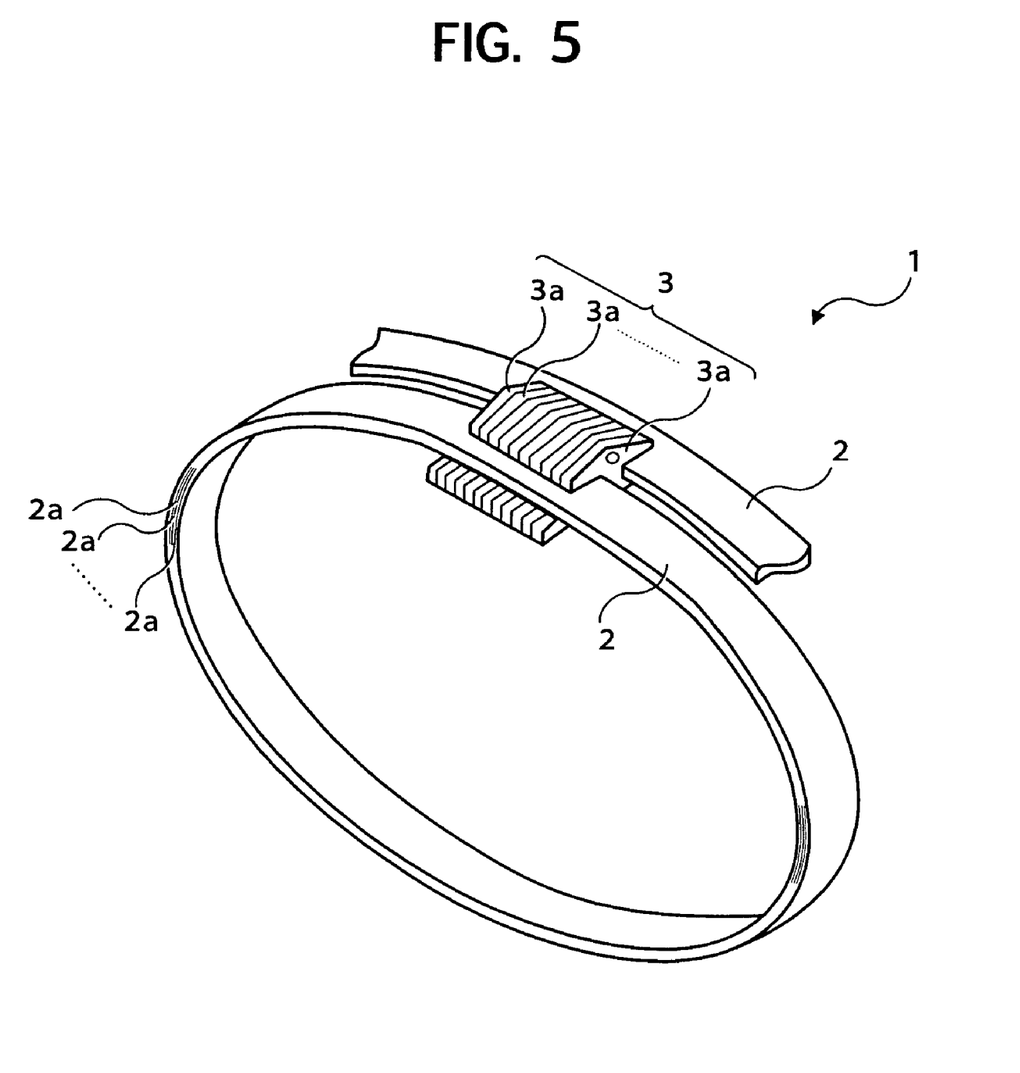
FIG. 5 is an outline view of a CVT belt.

FIG. 5 is an outline view of a CVT belt. FIG. 5 is an outline view of a CVT belt. In this diagram, a CVT belt 1 is constructed by assembling two laminated bands of a layered belt 2 that contain a stack of a number of metal rings 2a (for example, a laminated band composed of about 12 endless layers) which are supported by a layered element 3 composed of a large number of steel elements 3a (for example, about 400 elements).

In this manner, the structure of the CVT belt 1 is produced through the following processes:

(1) First, a ring-shaped drum is formed by welding together the ends of a thin sheet of ultrahigh strength steel, such as maraging steel.

(2) Next, the drum is cut into round slices of a predetermined width and rolled to create metal rings 2a of a basic peripheral length.

(3) Next, after performing a solution treatment, etc. to the above-mentioned metal rings 2a, the necessary peripheral length (namely, the peripheral difference between the inner and outer periphery) corresponding to the stacked layers of the CVT belt 1 using a "peripheral length correction device" is accomplished. Furthermore, aging treatment, nitride treatment, etc. are performed to increase the hardness of the metal rings 2a.

(4) Lastly, the metal rings 2a are laminated after undergoing the above-mentioned process (3), the steel elements 3a are consecutively attached and the CVT belt 1 is completed.

Naturally, since these metal rings 2a undergo the above-mentioned processes (such as manufacture of the drum, cutting, rolling, solution treatment, peripheral length correction, aging treatment, nitride treatment, etc.), partial defects occur, such as abrasions and indentations on the front and rear end faces of the metal rings 2a.

As an inspection method for such defects, there is a process for factory workers to determine the existence of abrasions, indentations, etc. by visually observing the front and rear end faces of the metal rings 2a preceding the CVT belt manufacturing process (4), namely by directly viewing parts or using a magnifying glass. However, in this antiquated method there is the drawback of being inefficient due to the fact that human error rate is always higher than an automated process. Thus, satisfactory reproducibility and reliability are not routinely acquired.

As for conventional prior art which is applicable to the surface inspection of the above-mentioned metal rings 2a, for example, Japanese Laid-Open Patent Application No. H11-248637 (1999) titled "DEFECT DETECTING DEVICE" (hereinafter denoted as "conventional prior art device") is known.

Particularly noteworthy, the principle configuration of this conventional prior art device comprises an inspection light source which illuminates the inspectable surface and at least two light guiding paths (optical fiber) which guide reflected light from the inspectable surface to the light reception segments, and the spacing arrangement of the two light guiding paths is separated at a slight distance. Thus, in such a configuration when an inspectable surface does not have a defect, etc., the reflected light guided by the two light guiding paths is supplied to the light reception segments at substantially the same intensity. On the other hand, when an inspectable surface has a minor defect, since there is a decline (light intensity decline by diffused reflection) in the reflected light of an applicable defective part, a difference occurs in the light of the light guiding paths and the existence of a defect can be automatically discriminated from the amount of this difference.

However, although the above-mentioned conventional prior art is a beneficial device from the viewpoint of being able to automatically discriminate whether or not a defect exists on an inspectable surface, there is a drawback in which the inspection process excessively detects for example "gloss marks" as manufacturing defects which do not impair the durability of the metal belt.

Also, a gloss mark is a type of flaw which makes no difference should some undoubtedly remain on the front and/or rear end faces of a metal belt as each is merely an abrasion. In nearly all cases, the entire abrasion is a smooth surface and the flaw does not impair the durability of a metal belt. Consequently, this type of flaw can be ignored as having no impact on the finished product. Thus, it is a waste of resources to exclude metal rings which have such a gloss mark as a defective part and not preferred in terms of manufacturing cost.

Therefore, the object of the present invention is to provide an inspection device for metal rings which does not perform excessive detection of a gloss mark as a detrimental flaw.

SUMMARY OF THE INVENTION

An inspection device for a metal ring of a Continuously Variable Transmission (CVT) V-belt related to the present invention comprises a light source for illuminating an inspectable surface of the metal ring to be inspected; a first light guiding path for guiding a reflected light from the inspectable surface to a first light detector and a second light guiding path for guiding the reflected light to a second light detector; a difference value calculation means for calculating a difference value between an electrical signal outputted from the first light detector or an electrical signal correlated to its electrical signal and an electrical signal outputted from the second light detector or an electrical signal correlated to its electrical signal; and a discrimination means for comparing the difference value with a predetermined threshold value and discriminating the existence of a defect on an inspectable surface. The difference value calculation means includes a first low-pass cutting means for cutting out a predetermined low-frequency component contained in an electrical signal outputted from the first light detector or an electrical signal correlated to its electrical signal and a second low-pass cutting means for cutting out a predetermined low-frequency component contained in an electrical signal outputted from the second light detector or an elec trical signal correlated to its electrical signal. In addition, the difference value calculation means calculates the difference value between an electrical signal which passes through the first low-pass cutting means and an electrical signal which passes through the second low-pass cutting means.

In the preferred embodiment of the present invention, the predetermined low-frequency component is an existing flaw on an inspectable surface and includes a frequency component signal which emerges corresponding to a flaw of no significance even if ignored among signals contained in an electrical signal outputted from the first light detector or an electrical signal correlated to its electrical signal and an electrical signal outputted from the second light detector or an electrical signal correlated to its electrical signal.

According to the present invention, although the discrimination means discriminates the existence of a defect on an inspectable surface by comparing two electrical signals outputted from the first and the second light detectors with a predetermined threshold value, a predetermined low-frequency component is not contained in the difference value. Also, this predetermined frequency component is preferably "the frequency component in which there is an existing flaw on an inspectable surface and occurs corresponding to an insignificant flaw that is not a hindrance even if disregarded among the signals contained in an electrical signal outputted from the first light detector or an electrical signal correlated to its electrical signal and an electrical signal outputted from the second light detector or an electrical signal correlated to its electrical signal." In this manner, the operation judges that there is no defect and avoids rejection as a defective part, such as defects (for example, gloss marks) which do not have a negative impact on the final product even if disregarded among the defects on an inspectable surface.

The above and further objects and novel features of the present invention will more fully appear from the following detailed description when the same is read in conjunction with the accompanying drawings. It is to be expressly understood, however, that the drawings are for the purpose of illustration only and are not intended as a definition of the limits of the invention.

DETAILED DESCRIPTION OF THE PREFERRED EMBODIMENTS

The preferred embodiments of the present invention will hereinafter be described in detail with reference to the drawings. Additionally, in the following explanation of specific or examples of various details, numerical values or character strings and other illustrative symbols are merely references to clarify the concept of the present invention. Accordingly, the concept of the present invention should not be limited explicitly to this terminology entirely or in part.

In addition, explanation is omitted which describes details of well-known methods, well-known procedures, well-known architecture, well-known circuit configurations, etc. (hereinafter referred to as "common knowledge") for the purpose of concise explanation, but does not intentionally exclude this common knowledge entirely or in part. Therefore, relevant common knowledge which is already known by persons skilled in the art at the time of filing the present invention is included in the following description.

Figure 1:
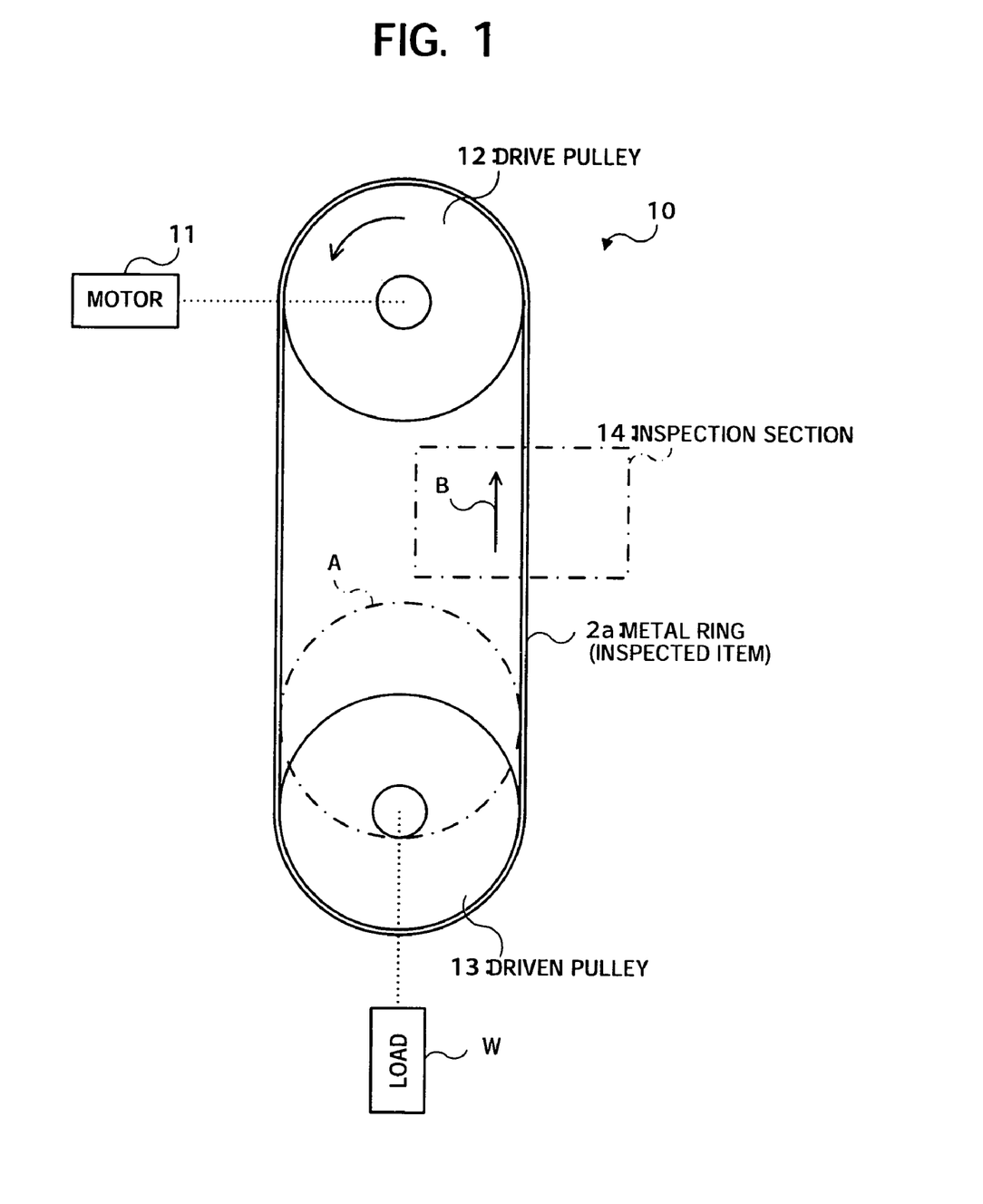
FIG. 1 is a conceptual line block diagram of an inspection device of a metal ring.

FIG. 1 is a conceptual line block diagram of an inspection device of a metal ring. An inspection device 10 comprises a fixed position drive pulley 12 which is rotary driven by a motor 11, a variable position driven pulley 13 which is separately situated on the same rotational plane as the drive pulley 12 and an inspection section 14.

When examining the metal rings 2a which are the object to be inspected, first, the driven pulley 13 is positioned at an initial position (refer to position "A" on the dashed dotted line). Subsequently, the metal rings 2a are wound around the two pulleys (drive pulley 12 and driven pulley 13). Next, the desired tension is applied to the metal rings 2a by supplying load W which has a predetermined mass (for example, 80 kg) and drives the driven pulley 13. In the state of while operating the motor 11 which causes the metal rings 2a to rotate unidirectionally (the direction of arrow "B") and with the inspection section 14, a front and rear end face inspection is performed.

Figure 2:
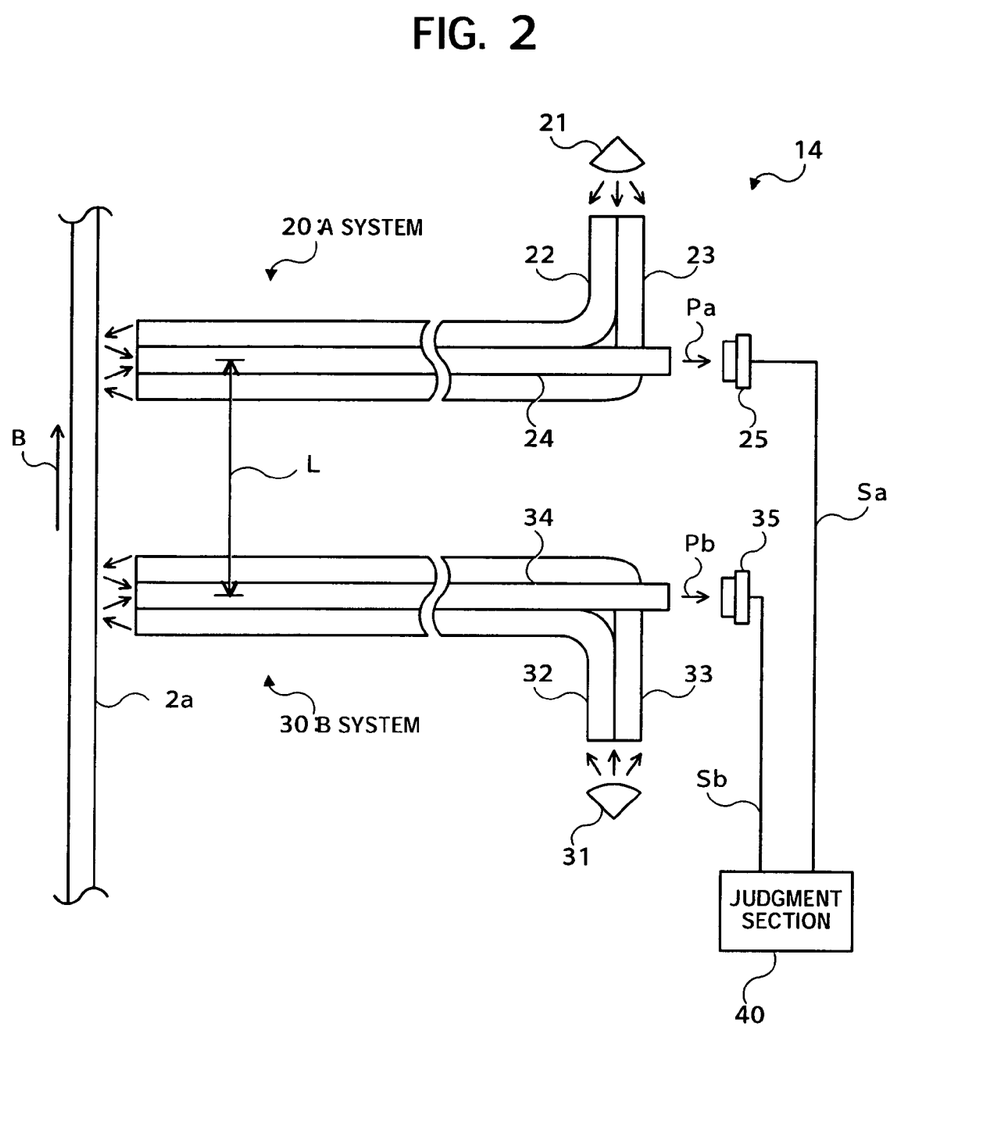
FIG. 2 is a conceptual line block diagram of an inspection section 14.

FIG. 2 is a conceptual line block diagram of the inspection section 14. Referring to this drawing, the inspection section 14 comprises at least two optical sensor sections 20 and 30 (hereinafter referred to as "A system optical inspection section 20" and "B system optical inspection section 30", or simply "A system 20" and "B system 30") and a judgment section 40. The reason for comprising "at least two" the optical sensor sections 20 and 30 is described later.

The A system 20 and B system 30 have the same configuration. Namely, the A system 20 (the B system 30) configuration includes two illuminating optical fibers 22 and 23 (32 and 33) for the purpose of guiding the light from a light source 21 (31) in parallel to the inspectable surface (here, although assumed as the "front end face" of the metal rings 2a, it may be the "rear end face") of an object to be inspected (the metal rings 2a); a light reception optical fiber 24 (34) inserted between the illuminating optical fibers 22 and 23 (32 and 33); and a light detector 25 (35) which converts reflected light Pa (Pb) into an electrical signal Sa (Sb) from the inspectable surface guided with the light reception optical fiber 24 (34). The light reception optical fiber 24 constitutes "a first light guiding path" mentioned earlier in the summary of the present invention and a light detector 25 which constitutes "a first light detector" also mentioned in the above summary. Additionally, the light reception optical fiber 34 constitutes "a second light guiding path" and a light detector 35 constitutes "a second light detector" both mentioned in the summary of the present invention.

The judgment section 40 judges whether or not a flaw exists on an inspectable surface of the metal rings 2a based on the electrical signal Sa outputted from the light detector 25 of A system 20 and the electrical signal Sb outputted from the light detector 35 of the B system 30. The basic principle as also described in the opening patent document 1 pertains to "the intensity of the light which enters into the two light detectors 25 (35) is substantially the same when an inspectable surface does not contain a defect and differs when there is a defect". Also, "the difference value of the electrical signals Sa and Sb outputted from the two light detectors 25

(35) is acquired. When this difference value is greater, this is indicative that the inspectable surface contains a defect and will be discriminated".

In other words, when an inspectable surface of the metal rings 2a does not have a defect, the inspectable surface is a smooth surface and the light from the illuminating optical fibers 22 and 23 (32 and 33) is equally reflected in terms of being smooth and diffused reflection is hardly generated. Accordingly, the intensity of the light which enters into the light detectors 25 (35) is composed of the appropriate strength and substantially the same amount. In this case, the difference value of the electrical signals Sa and Sb are practically set to "0".

On the other hand when the inspectable surface of the metal rings 2a has a defect, the light from the illuminating optical fibers 22 and 23 (32 and 33) will reflect diffusely at the defective spot. Thus, the intensity of the light guided to the light detector 25 (35) via the light reception optical fiber 24 (34) only decreases by the percent age of diffused reflection. In this case, the spacing of the A system 20 and the B system 30 is separated only by distance L. If this distance L is suitably greater than the above-stated defect size, when the light reception optical fiber of one system (for example, the light reception optical fiber 24 of A system 20) guides light declined in strength by the influence of a defect, the light reception optical fiber (light reception optical fiber 34 of B system 30) of the system on the other side will guide light not declined in strength (namely, intense reflected light strength from a smooth surface without a defect). Consequently, in this case, because the electrical signal Sa becomes less than (<) the electrical signal Sb, the difference value clearly becomes greater as compared with the above-mentioned normal condition (Sa=Sb).

The above principle can be applied as in "when the electrical signals Sa and Sb are outputted from the two light detectors 25 (35), the difference in values is calculated and a greater difference indicates an inspectable surface has a defect which can be discriminated".

The reason at least two systems (the A system 20, the B system 30) are required is as follows: based on the above-stated principal explanation, when an inspectable surface does not contain a defect the electrical signal Sa (or Sb) outputted from either of the systems constitutes a "greater value". Subsequently, when an inspectable surface contains a defect, while either system is receiving reflected light (declined light strength only by the percentage of diffused reflection) from a defect, the electrical signal Sa (or Sb) outputted from that system constitutes a "lesser value."

In the above principle, a judgment is possible by recognizing these "greater values" and "lesser values." However, the surface of the metal rings 2a used in a CVT belt as an object to be inspected is in most cases delustered (dull finish) and because the degree of delustering is not standard for each product (or lot), variations occur in the "greater value" of the electrical signal Sa (or Sb) which serves as the standard for normal judging. The influence of the above-stated variations can be eliminated by configuring the optical sensor sections with "at least two systems" and taking the "difference value" between the electric signal Sa (and Sb) outputted from those systems.

Figure 3:
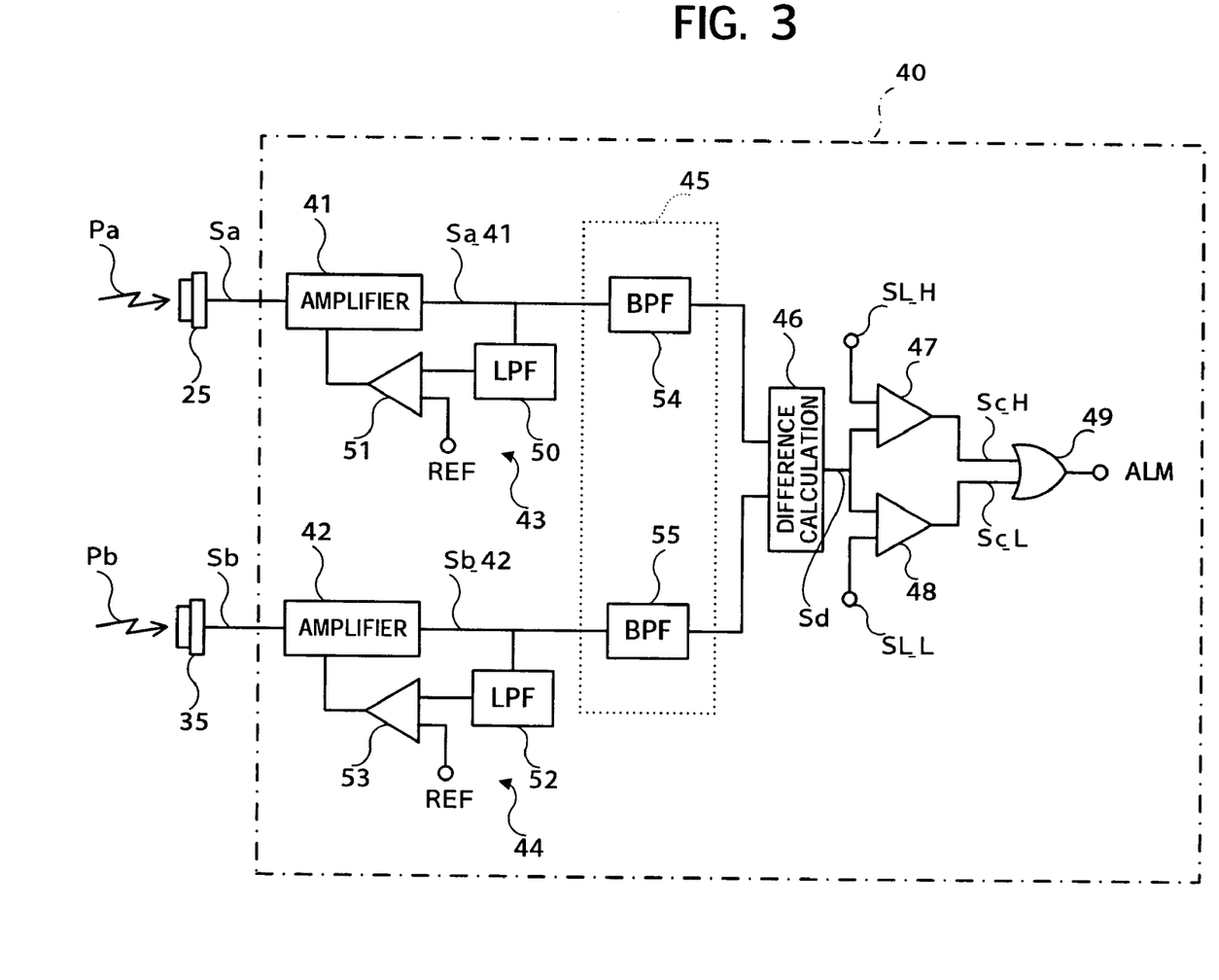
FIG. 3 is a block diagram of a judgment section 40.

FIG. 3 is a block diagram of the judgment section 40. Referring now to this drawing, the judgment section 40 configuration includes an amplifier 41 for A system, an amplifier 42 for B system, an AGC circuit 43 for A system, an AGC circuit 44 for B system, a band pass filter section 45, a difference calculation section 46 (difference value calculation means), a high side threshold value judgment section 47 (discrimination means), a low side threshold value judgment section 48 (discrimination means), and an alarm signal generation section 49.

The amplifier 41 for A system amplifies the electrical signal Sa which is outputted from the light detector 25 of the A system and fluctuation control of the amplification factor is performed by the output of the AGC circuit 43 for A system. The AGC circuit 43 for A system includes a low-pass filter 50 which extracts only a low-frequency component contained in the continuous current from among the output signals of the amplifier 41 for A system and a differential amplifier 51 which generates the AGC voltage of the amount corresponding to the difference between the output of the low-pass filter 50 and a predetermined reference voltage REF. The amplifier 41 for A system amplifies the electric signal Sa by the amplification factor corresponding to this AGC voltage. The purpose of this AGC voltage is to remove low-frequency component "fluctuations" (generated in connection with "surface blurring" of the metal rings 2a) contained in the electrical signal Sa.

The amplifier 42 of B system like the above-stated amplifier 41 for the A system amplifies the electrical signal Sb outputted from the light detector 35 for the B system and fluctuation control of the amplification factor is performed by the output of the AGC circuit 44 for B system. The AGC circuit 44 for the B system includes a low-pass filter 52 which extracts only a low-frequency component contained in continuous current from among the output signals of the amplifier 42 for B system and a differential amplifier 53 which generates the AGC voltage of the amount corresponding to the difference between the output of the low-pass filter 52 and a predetermined reference voltage REF. The amplifier 42 for B system amplifies the electrical signal Sb by the amplification factor corresponding to this AGC voltage. The purpose of this AGC voltage is the same as that above which is to remove low-frequency component "fluctuations" contained in the electrical signal Sb.

The band pass filter section 45 is an integral part which is essential in the present invention. However, initially a case "when not provided" with the band pass filter section 45 will be explained. Then, after describing its drawback, the configuration of the present invention (a configuration which does provide the band pass filter section 45) will be explained.

First, the difference calculation section 46 calculates a difference value Sd between an electrical signal Sa_41 outputted from the amplifier 41 for A system and an electrical signal Sb_42 outputted from the amplifier 42 for B system. The high side threshold value judgment section 47 compares the difference value Sd with a predetermined high side threshold value SL_H and outputs a high side determination result signal Sc_H which becomes active when Sd is greater than SL_H (Sd>SL_H). The low side threshold value judgment section 48 compares the same difference value Sd with a predetermined low side threshold value SL_L and outputs a low side determination result signal Sc_L which becomes active when Sd is greater than SL_L (Sd>SL_L). In addition, the alarm signal generation section 49 outputs an alarm signal ALM which indicates a defect detection on an inspectable surface when either of these two determination result signals (SL_H, SL_L) become active.

Figure 4A:
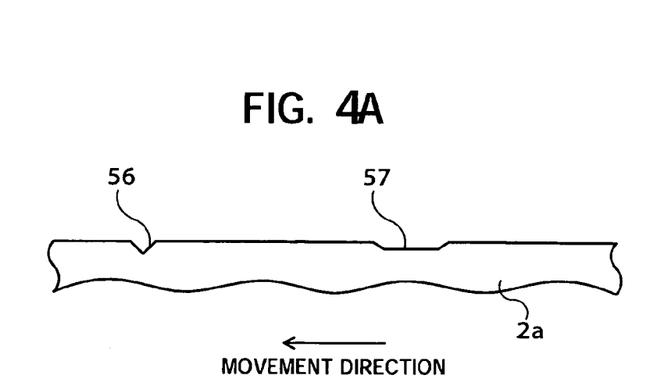
FIGS. 4A, 4B, and 4C are cross sectional plan views of a metal rings 2a and waveform diagrams of an output signal (difference value Sd) from a difference calculation section 46.
Figure 4B:
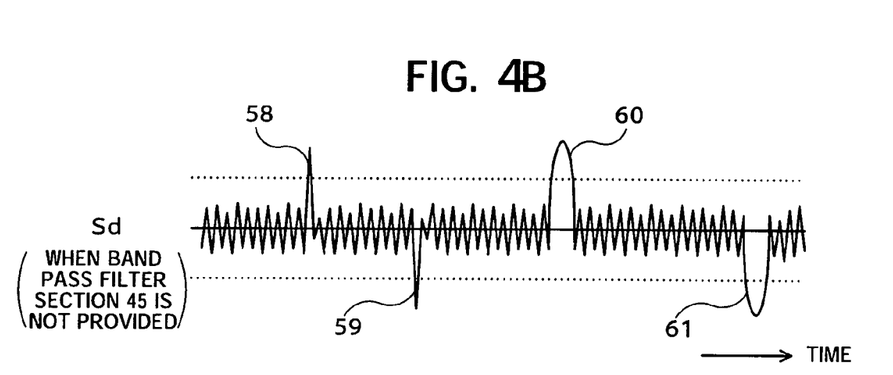

FIG. 4A is a cross sectional plan views of the metal rings 2a which has a flaw 56 which should be detected as a defect and a gloss mark 57 which has no significant impact on producing a product without imperfections and can be ignored (disregarded). FIG. 4B is waveform diagram of the output signal (difference value Sd) of a difference calculation section 46 in the case of not providing the band pass filter section 45.

In FIG. 4B, the difference value Sd composed of a normal region which does not exceed the two threshold values (SL_H and SL_L) and an abnormal region which exceeds one of the threshold values. At the beginning part on the time axis are two abnormal regions which are illustrated by a peak signal waveform 58 and 59. These appear corresponding to a flaw 56 which should be detected as a defect. The distance between these two signal waveforms 58 and 59 corresponds to the distance L of the two optical sensor sections 20 and 30 for the A system and the B system.

In the case of such a waveform diagrams, the high side determination result signal Sc_H becomes active in response to the signal waveform 58 and the low side determination result signal Sc_L becomes active in response to the other side signal waveform 59. In either of these cases, the alarm signal ALM is outputted which indicates detection of a defect on an inspectable surface. Furthermore, included in this waveform diagram are the peak signal waveforms 60 and 61 which correspond to a gloss mark 57 that can be ignored and contained in the difference value Sd. Because both of these signal waveforms 60 and 61 exceed the threshold values (SL_H and SL_L), the high side determination result signal Sc_H becomes active in response to the signal waveform 60 and the low side determination result signal Sc_L becomes active in response to the other side signal waveform 61. There is a drawback in that the alarm signal ALM which indicates defect detection on an inspectable surface will also be outputted for the gloss marks 57 which are not imperfections and can be omitted.

Consequently, the inventors of the present invention have focused on the difference between the frequency components of the two types of signal waveforms above (the peak signal waveforms 58 and 59 corresponding to a flaw 56 which should be detected as a defect and the peak signal waveforms 60 and 61 corresponding to a gloss mark 57 that can be ignored). In detail, the latter signals (the peak signal waveforms 60 and 61 corresponding to a gloss mark 57 that can be ignored) contain relatively a low frequency component than the first signals (the peak signal waveforms 58 and 59 corresponding to a flaw 56 which should be detected as a defect). The above-described drawback (output of the alarm signal ALM which indicates the detection of a defect on an inspectable surface relative to gloss marks 57 that can be ignored) can be eliminated by providing the band pass filter section 45 for cutting out (extracting) the low frequency component in the preceding stage relative to the difference calculation section 46.

Accordingly, the distinctive characteristic of the configuration in the present invention is as shown in FIG. 3. Specifically, the band pass filter section 45 composed of the band pass filter 54 for A system (first low-pass cutting means) and the band pass filter 55 for B system (second low-pass cutting means) are provided in the preceding stage relative to the difference calculation section 46. The throughput characteristic of the band pass filter 54 for A system and the band pass filter 55 for B system from the above explanation is "the characteristic which allows throughput of the peak signal waveforms 58 and 59 corresponding to actual flaws 56 and conversely does not allow throughput of the peak signal waveforms 60 and 61 corresponding to gloss marks 57 which are not imperfections."

The preferable characteristic is a inspection device, for example, for cutting out the low-frequency component of about 100 Hz or less.

Figure 4C:
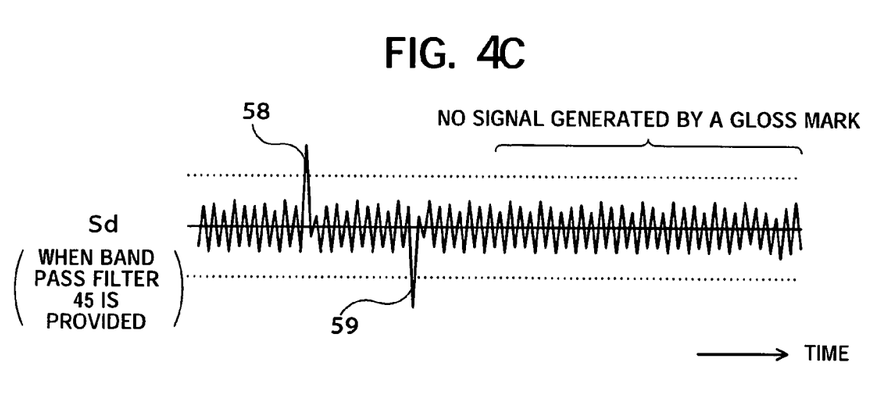

FIG. 4C is a waveform diagram of the output signal (the difference value Sd) of the difference calculation section 46 in the case of providing the band pass filter section 45 (according to the configuration of the present invention). In this waveform diagram, the difference value Sd is composed of a normal region which does not exceed the two threshold values (SL_H and SL_L) and an abnormal region which exceeds one of the threshold values. The abnormal regions are only the peak signal waveforms 58 and 59 which appear corresponding to a flaw 56 which should be detected as a defect and the peak signal waveforms (the waveforms 60 and 61 in FIG. 4B) corresponding to ignorable gloss marks 57 are not included. This is because the signal waveforms (the waveforms 60 and 61 in FIG. 4B) corresponding to the gloss marks 57 are removed by the band pass filter 54 for A system and the band pass filter 55 for B system provided in the preceding stage relative to the difference calculation section 46.

Therefore, according to this configuration, the alarm signal ALM which indicates defect detection on an inspectable surface in response to only the peak signal waveforms 58 and 59 related to an actual flaw 56 which should be detected as a defect. Thus, the alarm signal ALM output will not be performed relative to gloss marks 57 that can be ignored. As a result, not to mention metal rings 2a that have neither no flaws 56 nor any gloss marks 57, but also metal rings 2a that have only gloss marks 57 will be considered as acceptable when inspected. The present invention will significantly help prevent wasted material and reduce manufacturing costs.

Furthermore, the present invention is not limited to the above-stated embodiment. Within the scope of the technical concept, naturally various modifications or future development cases are included. For example, the present invention may be adapted as follows:

Although, in the above-mentioned embodiment, the inspectable surface is expressed as the "front end face" of the metal rings 2a, it may be expressed as "the rear end face" of the same ring.

Moreover, in the above-mentioned embodiment, although the light from the light source 21 (31) are guided to an inspectable surface through the illuminating optical fibers 22 and 23 (32 and 33), they are not restricted to this example. The light from the light source 21 (31) may directly irradiate an inspectable surface or irradiate a surface via an optical element, such as an optical lens.

Besides, in the above-stated embodiment, although the optical sensor section is formed by two systems (the A system 20 and the B system 30), it may be configured with multiple systems exceeding two. Also, when configured with multiple systems more than two, each system may be situated on the periphery direction and width direction of the metal rings 2a (a two-dimensional array).

Lastly, in the above-mentioned embodiment, although the reflected light from an inspectable surface is guided to the light detector 25 (35) via the light reception optical fiber 24 (34), the use of this "optical fiber" merely indicates the best mode of the embodiment. In brief, what is necessary is just a "light guiding object" which can guide reflected light from an inspectable surface to the light detector 25 (35) with the smallest possible intensity loss. For example, if intensity loss and flexibility are disregarded or ignored, the light guiding object may simply be made out of glass or plastic.

While the present invention has been described with reference to the preferred embodiments, it is intended that the invention be not limited by any of the details of the description therein but includes all the embodiments which fall within the scope of the appended claims.

What is claimed is:

1. An inspection device for metal rings of a Continuously Variable Transmission (CVT) V-belt comprising:
    a light source for illuminating an inspectable surface of said metal rings to be inspected;
    a first light guiding path for guiding a reflected light from said inspectable surface to a first light detector and a second light guiding path for guiding said reflected light to a second light detector;
    a difference value calculation means for calculating a difference value between an electrical signal outputted from said first light detector or an electrical signal correlated to its electrical signal and an electrical signal outputted from said second light detector or an electrical signal correlated to its electrical signal; and
    a discrimination means for comparing said difference value with a predetermined threshold value and discriminating the existence of a defect on said inspectable surface;
    said difference value calculation means includes:
    a first low-pass cutting means for cutting out a predetermined low-frequency component contained in an electrical signal outputted from said first light detector or an electrical signal correlated to its electrical signal and
    a second low-pass cutting means for cutting out a predetermined low-frequency component contained in an electrical signal outputted from said second light detector or an electrical signal correlated to its electrical signal; and
    said difference value calculation means calculates said difference value between an electrical signal which passes through said first low-pass cutting means and an electrical signal which passes through said second low-pass cutting means.

2. The inspection device for metal rings according to claim 1, wherein said predetermined low-frequency component is an existing flaw on said inspectable surface and includes a frequency component signal which occurs corresponding to a flaw of no significance even if ignored among signals contained in an electrical signal outputted from said first light detector or an electrical signal correlated to its electrical signal and an electrical signal outputted from said second light detector or an electrical signal correlated to its electrical signal.

* * * * *